United States Patent [19]

Bente et al.

[11] Patent Number: 4,714,545
[45] Date of Patent: Dec. 22, 1987

[54] FLUID PROPORTIONING PUMP SYSTEM

[75] Inventors: H. Bryan Bente; Alan C. Herman, both of Half Moon Bay; Joel Myerson, Berkeley; Benjamin G. Shaw, Palo Alto; Andrew Stefanski, Menlo Park, all of Calif.

[73] Assignee: Hewlett-Packard Company, Palo Alto, Calif.

[21] Appl. No.: 841,922

[22] Filed: Mar. 20, 1986

[51] Int. Cl.$^4$ .................... B01D 15/08; F04B 41/06
[52] U.S. Cl. ................... 210/101; 210/198.2; 417/5
[58] Field of Search ............ 210/101, 198.2; 417/3–5, 18, 22

[56] References Cited

U.S. PATENT DOCUMENTS

| | | | |
|---|---|---|---|
| 3,917,531 | 11/1975 | Magnussen | 210/198.2 |
| 4,043,906 | 8/1977 | Helmer | 210/198.2 |
| 4,128,476 | 12/1978 | Rock | 210/101 |
| 4,311,586 | 1/1982 | Baldwin et al. | 210/101 |
| 4,321,014 | 3/1982 | Eburn, Jr. et al. | 417/5 |

*Primary Examiner*—Richard V. Fisher
*Assistant Examiner*—Richard D. Jordan
*Attorney, Agent, or Firm*—Edward Y. Wong

[57] ABSTRACT

A plurality of different liquid solutions are connected to an input of a pump system having at least two displacement chambers and in a manner to control the proportions of each constituent that are taken into each chamber during its intake stroke. The outputs of the chambers are connected to a common liquid output. The chambers are driven by independently controllable motors so that the discharge stroke may be chosen to have some parameters, such as speed profile and duration, that are different than during the intake stroke. As a result, both chambers may simultaneously discharge liquid through the common output, if desired. The proportion of constituents may be made different each time one of the chambers is filled, so the simultaneous discharge of the chambers allows a gradual, carefully controlled change from the mixture of one chamber to that of the other. Thus, the pump system can be operated to provide a combination of low pressure and high pressure mixing of two or more liquid constituents in order to provide a smooth gradient in the output liquid flow. Output liquid flow rate can be controlled by changing the time in which the chamber's volume is reduced, or by controlling the maximum volume of the chamber's displacement, or both. Such a pumping system is especially useful in providing a solvent mixture with a gradually changing composition to a liquid chromatograph column.

9 Claims, 6 Drawing Figures

FLUID PROPORTIONING PUMP SYSTEM

BACKGROUND OF THE INVENTION

This invention relates generally to a fluid supply system, and more specifically to a pumping system that delivers a controlled mixture of two or more constituents of liquid, being especially adapted for use in a liquid chromatograph as a mixing pump supplying solvent to a separation column.

The requirements of a mixing pump system in a liquid chromatograph are very stringent. Liquid flow into its separation column must have a substantially uniform flow rate and liquid pressure. Further, in gradient chromatography, the composition of the liquid so supplied must be gradually altered over time. Separate liquid constituents are mixed together in varying relative concentrations over time by the mixing pump system.

There are basically two categories of liquid mixing pumps that have previously been used for such an application. One category is known as a high pressure mixing pump system, and the other category is known as a low pressure mixing pump system.

In the high pressure mixing pump system, each liquid constituent, or component, to be mixed is connected from a reservoir of that component to an input of its own liquid pump. That is, each component is put under pressure by its own dedicated pump, and the outputs of each of the component pumps are joined together to form the output of the mixing pump system that is connected to the separation column of a liquid chromatograph, in that particular application. The flow rate of each pump is adjusted to provide the right proportions of the liquid components in its output, and to control the total flow velocity in that output. A usual application requires the proportions of the components to change over time, termed "gradient" flow, which requires the flow rates of the individual pumps to be appropriately changed over time to accomplish this. For example, if two components are being supplied in the mixing pump output with the percentage of one component increasing over time and that of the other component decreasing, the respective pumps for these components have their flow rates respectively increased and decreased over time in order to alter the balance of component concentrations without changing the total output flow rate.

A significant disadvantage of high pressure mixing systems is that a separate pump is required for each solvent or other liquid component that is being mixed. In some cases, more than two such components must be mixed. In the liquid chromatograph supply application particularly, the pumps must be of high precision and thus are very expensive. Typically, each such pump includes two displacement chambers, or syringes, that are operated approximately 180° out of phase so that one pump chamber is discharging fluid while the other is charging. This category of high pressure system has a significant operating advantage, however, in that the component concentration in the output flow can be smoothly varied over time since each of the component pumps can have their flow rate independently adjusted.

The second category of mixing pump systems is termed a low pressure type. In this type, a single pump is utilized with each of the solvents, or other liquid components, connected from their separate sources to the input of the pump. Dual displacement chambers, or syringes, are generally used to make up this pump. Each liquid component supply is connected to the intake of the pump through a control valve. The pump is operated so that when a displacement chamber is being charged, each liquid component control valve is turned on for a portion of the charging part of the cycle. That is, in the usual case of a piston type displacement chamber, the valve of one constituent supply is opened for a first part of the intake stroke of the piston, it is then closed, and a valve of a second liquid component supply is opened for a time, and so forth, for each of the components that are to be mixed. While one displacement chamber is being charged with a mixture of components in a particular proportion, the other displacement chamber is discharging its previously mixed liquid. The two pistons of the two displacement chambers are mechanically connected to operate essentially 180° out of phase with each other. The result is a liquid output whose composition changes in a step function fashion; that is, when the particular mixture in one chamber is completely discharged, the next chamber begins to discharge a mixture which usually is different in its percentage of liquid components. Thus, there is a sudden change in the proportion of components of the mixture when the discharge of one pump chamber ends and the other begins.

An advantage of the low pressure category of mixing pump systems is that only one pump with a pair of displacement chambers is required, in combination with appropriate intake valving of the various liquid component supplies, thereby minimizing the complexity and cost of a high precision pumping system. A disadvantage, however, of this category of mixing pumps, is its limited output flow rate range. The maximum flow rate is limited by the switching speed of the component liquid intake valves. As the output flow rate increases, the speed of the pump has to increase, which results in the intake stroke time being reduced. At some point, the intake stroke time becomes too short for the inlet valves to switch with enough control to provide the precise proportions of components desired during the short intake stroke.

The low pressure mixing systems also have a lower limitation of output flow. As the flow rate of such a pumping system decreases, the time for the delivery stroke becomes very long. Since the composition of the various liquid components in the displacement chamber is not changed during each discharge stroke, the pump system output composition has to remain the same for the duration of the delivery of each discharge stroke. The slower the pump operates, the longer is the duration of discharge of a particular fixed mixture. Since such a mixing pump system is usually utilized where the output mixture is desired to have a gradual change in relative concentrations of its components, there is some limit as to how long this period of constant output mixture can be tolerated. Thus, this places a lower limit on the flow rate available from the low pressure category of pumps.

Some improvements have been made in the operation of both categories of pumps by paying attention to the mechanical drive interconnection between the pistons of the two displacement chambers. Rather than operating exactly 180° out of phase with the other, such linkages have been provided so that the common motive source of the pump provides a slightly longer discharge time of each chamber than its intake time. The reason for this is to smooth out the liquid flow rate by avoiding any discontinuities when one displacement chamber ends its discharge stroke and the other begins. In many applications, such as in the liquid chromatograph, a flow of uniform velocity and pressure is quite important. But such improvements have not addressed the more basic limitations of such pumping systems that are described above.

Therefore, it is a primary object of the present invention to provide a fluid mixing pump system that is mechanically simple, and thus of a lower cost, but which provides a liquid output that smoothly and accurately varies the composition of the fluid output over a wide range of pump output flow rates.

Another object of the present invention is to provide a mixing pump system that may be adapted for a wide variety of specific applications and requirements.

SUMMARY OF THE INVENTION

These and additional objects are accomplished by the various aspects of the present invention, wherein, briefly, a single pump of at least two displacement chambers is provided wherein each chamber is separately driven in a manner that is independent of the other. In a preferred form of the invention, each displacement chamber includes a piston that is driven by a separate electrical motor. The motors are in turn controlled by appropriate control electronics in order to provide desired predetermined relative operation of the pistons. The fluid components to be mixed are connected to the intakes of the displacement chambers through electrically operated valves that are also controlled by the control electronics. The outputs of the displacement chambers are connected together to form a common pump output. The structure of the pumping system is similar to that of the low pressure category of pumps discussed above, except that its driving pistons are no longer connected to a common motor drive source but rather have been mechanically uncoupled from each other so that they may be independently operated.

It has been discovered that independent control of the intake and discharge portions of the piston cycle can lead to some very beneficial improvements in the smoothing of the change (gradient) of the output liquid mixture. According to one specific aspect of the present invention, the intake portion of the cycle is made a fixed duration of time for any discharge flow rate over a wide range. The fixed intake time allows the inlet valves to be operated in the same manner independent of the output flow rate of the pumping system.

In one specific form of the fixed intake time feature of the present invention, the piston stroke distance is made larger and its velocity is increased, so the pump cycle time remains the same when the flow rate output is desired to be increased. Existing mechanical linkages of the pistons do not allow varying the piston stroke length, but an independent motor drive does. A significant added advantage of this improved operation is that the duration of time during which the output has an unchanging mixture also remains the same, no matter what the output flow rate; that is, the duration of the steps in mixture of the liquid components is held fixed in time as the pump flow rate is increased. This is not the case with existing low pressure mixing pumps where the steps of constant mixture output increase in duration as the flow rate decreases, making the output gradient depart further from the desired continuous function.

In another specific form of the fixed intake time aspect of the present invention, the stroke is held constant and the piston velocity profile is the same on each intake stroke over the full range of output flow rates. In this case, the discharge portion of the stroke is controlled, independent of the intake stroke, to provide the desired output flow rate. The discharge portion of the cycle is made to take more time than that of the fixed intake portion, as the flow decreases, so there is a significant overlap wherein both displacement chambers are simultaneously discharging fluid into their common output. This allows a gradual change in the pump output from the mixture of one displacement chamber to that of the other. This combines the best features of both the low pressure and high pressure types of mixing pump systems. The time that the mixture in the pump output has to be that of a single displacement chamber is the fixed time of the intake stroke; this time does not increase as the output flow rate is decreased.

Additional objects, advantages and features of the various aspects of the present invention will become apparent from the following description of its preferred embodiment, which description should be taken in conjuction with the accompanying drawings.

DESCRIPTION OF THE PREFERRED EMBODIMENTS

Figure 1:
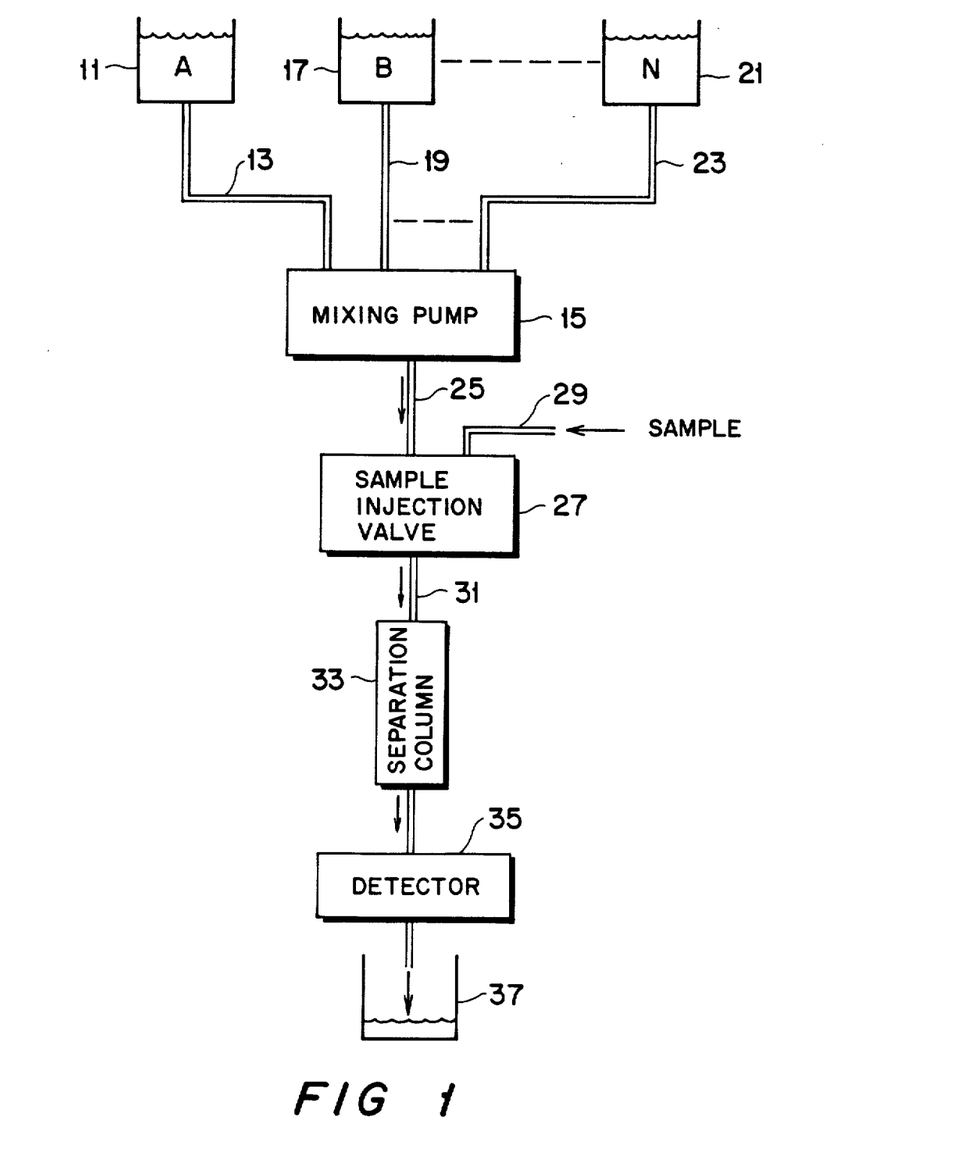
FIG. 1 illustrates a liquid chromatograph that utilizes the improved mixing pump techniques of the present invention.

Referring initially to FIG. 1, a liquid chromatography system is schematically illustrated for the purpose of showing one very specific application of the mixing pump improvements of the present invention. A container 11 of a liquid solvent A is connected by a supply tube 13 to a mixing pump system 15. Similarly, a second container 17 holds a different solvent B that is connected to the mixing pump 15 through a conduit 19. In some applications, only two solvents A and B are used. In other applications, however, additional solvents are utilized, an indefinite additional number being illustrated by another container 21 of the Nth solvent that communicates by a conduit 23 with the mixing pump 15.

The mixing pump 15 mixes the input solvents in a predetermined manner to be explained hereinafter, and delivers the mixture under pressure in a conduit 25. For a liquid chromatograph instrument, it is important that the flow in the output conduit 25 be of uniform velocity and pressure. That flow passes through a sample injection valve 27, that introduces a small liquid sample therein that is applied through a sample tube 29. The combined solvent with sample is then delivered through a tube 31 to a separation column 33, a primary element of a standard chromatograph. As is well known, the separation column includes beads that are coated with a composition that retains the sample material from the flow in the conduit 31.

A gradual change in the composition of the solvent liquid that is applied to the column 33 liberates different constituents of the sample material from the beads at different times. It is the mixing pump 15 that causes the composition of the solvent flow through the separation column 33 to change over time in a precise, predetermined way. The solvent with sample material is then passed through a detector 35. The presence of quantities of sample material constituents at different times tells the analyst the composition of the sample material originally injected into the tube 29. The liquid is then discharged from the detector into a container 37. That liquid can be considered as waste, and discarged, or can be collected in separate containers at the times that the different sample constitutents are being discharged from the column 33.

Figure 2:
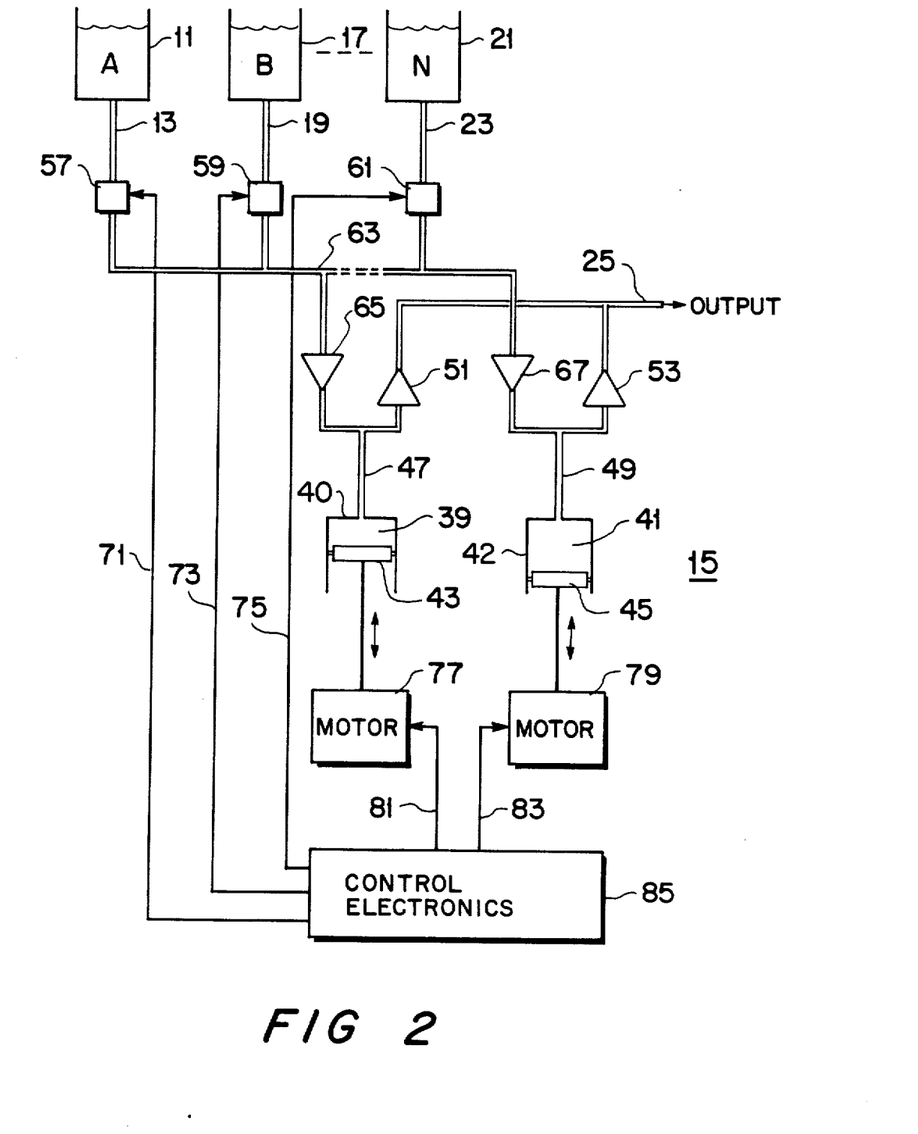
FIG. 2 shows the physical structure of the improved mixing pump of the present invention.

Referring to FIG. 2, the mixing pump 15, utilizing the various aspects of the present invention is described. At the heart of the pumping unit are two displacement chambers 39 and 41. Each displacement chamber contains, in this embodiment, cylinders 40 and 42, and pistons 43 and 45 respectively. The pistons are operated to control the volumes of their respective chambers. The two displacement chambers are connected in parallel. That is, the discharge from each of the chambers 39 and 41 passes through their respective outlet conduits 47 and 49, through their respective check valves 51 and 53, and into the single liquid output conduit 25. Similarly, liquid inputs in the conduits 13, 19 and 23 are applied through their respective valves 57, 59 and 61, to a common intake conduit 63. The liquid openings 47 and 49 to the two displacement chambers 39 and 41, respectively, receive liquid from the common input conduit 63 through their respective input check valves 65 and 67. Alternatively, check valves 51, 53, 65 and 67 could be replaced by actively driven valves.

The valves 57, 59 and 61 may be individual valves that are electrically controlled by signals in control lines 71, 73 and 75, respectively. Alternatively, a single mechanical proportioning valve may be substituted for the individual valves 57, 59 and 61. In either case, the purpose of the input valves is to connect one liquid solvent at a time to a displacement chamber that is being charged. For example, withdrawal of the piston 43 in the chamber 39 will cause fluid to flow through the check valve 65 into the chamber 59, the fluid so flowing being chosen by connecting one of the conduits 13, 19 or 23 at a time into the common input line 63.

Instead of driving the pistons 43 and 45 from a fixed mechanical drive and a single motor, as is the predominant structure of existing mixing pumps, a separate electric motor 77 is provided for driving the piston 43, and another separate motor 79 is provided for driving the piston 45. Each of these motors may be chosen from among those readily available, such as a stepper motor or a direct current motor with a servo feedback control added. In any case, each of the motors is chosen to be of a type that can accurately and predictably position its respective piston within its respective displacement chamber. Control signals for the motors are provided in circuits 81 and 83, respectively. Suitable control electronics 85 are designed to provide the appropriate signals in the lines 71, 73, 75, 81 and 83 in order to cooperatively move the pistons and open the intake valves in order to operate the pump system of FIG. 2 in a particular, predetermined manner.

Two such particular operable configurations for the pump of FIG. 2 are illustrated in FIGS. 3 through 6.

Figure 3:
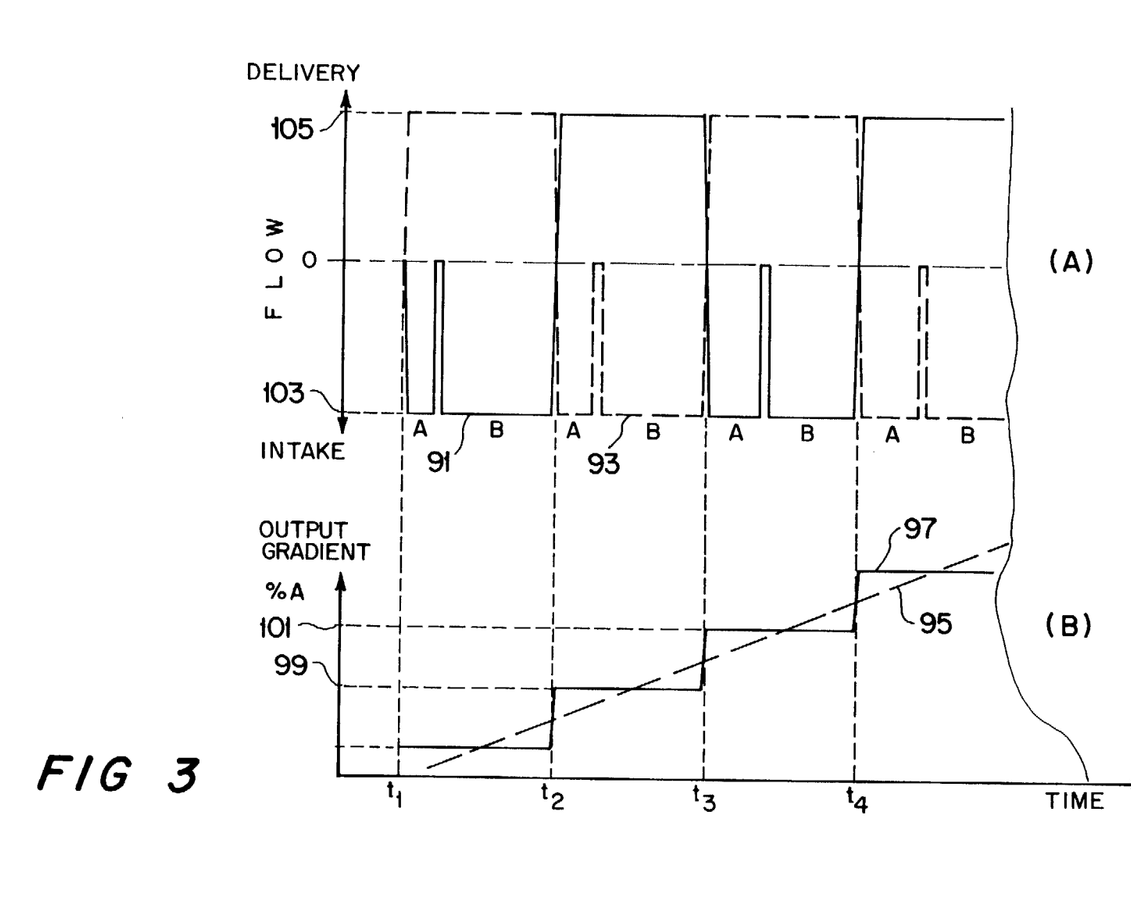
FIGS. 3 and 4 are curves that illustrate the operation of the mixing pump of FIG. 2, according to one specific embodiment thereof.
Figure 4:
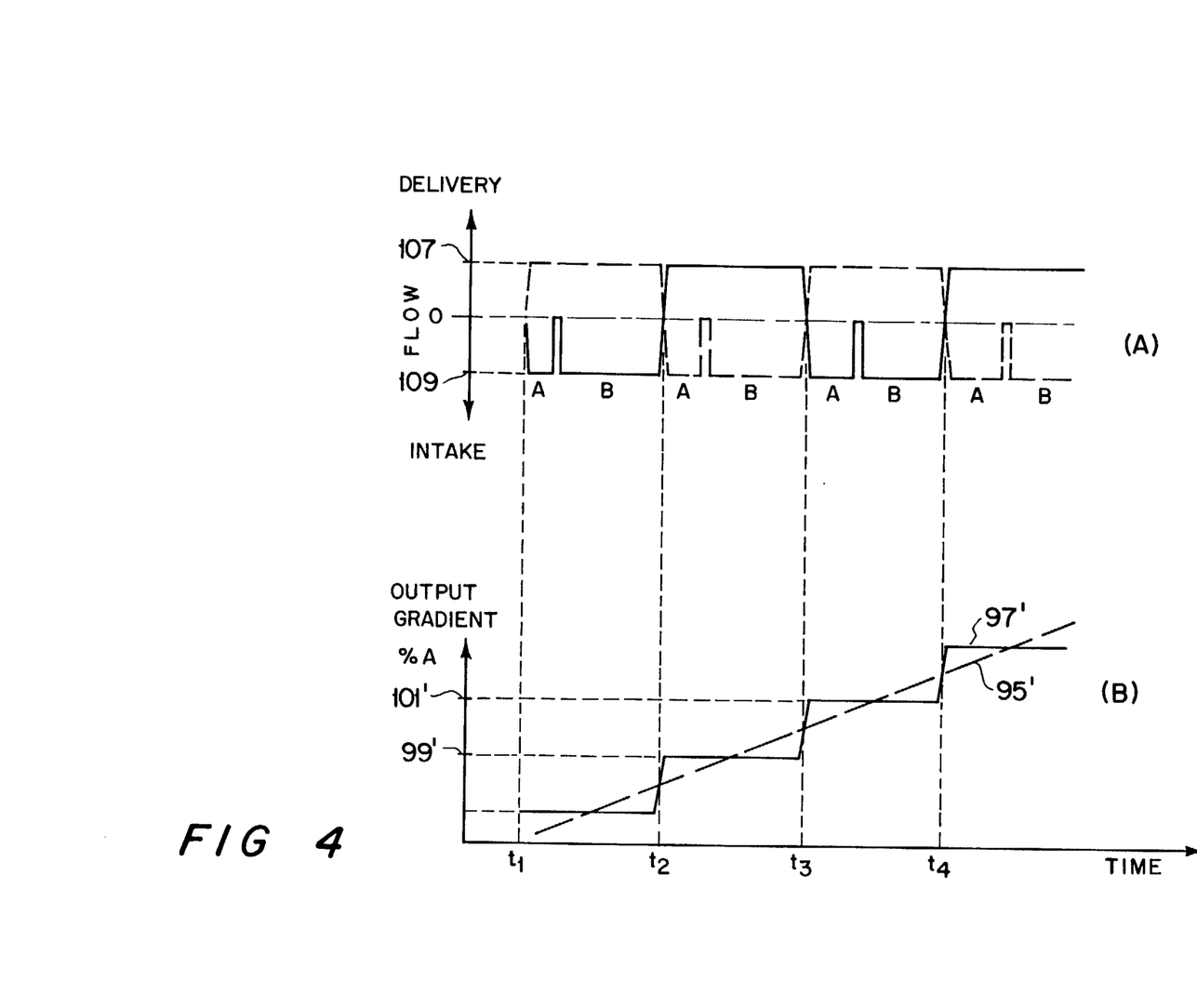

FIGS. 3 and 4 illustrate an operable configuration where the displacement of the pistons 43 and 45 is altered when it is desired to change the flow rate in the output 25 of the pump. The piston stroke of existing pumps cannot be changed because they are driven from a common motor source through an interlocked mechanical system.

Figure 5:
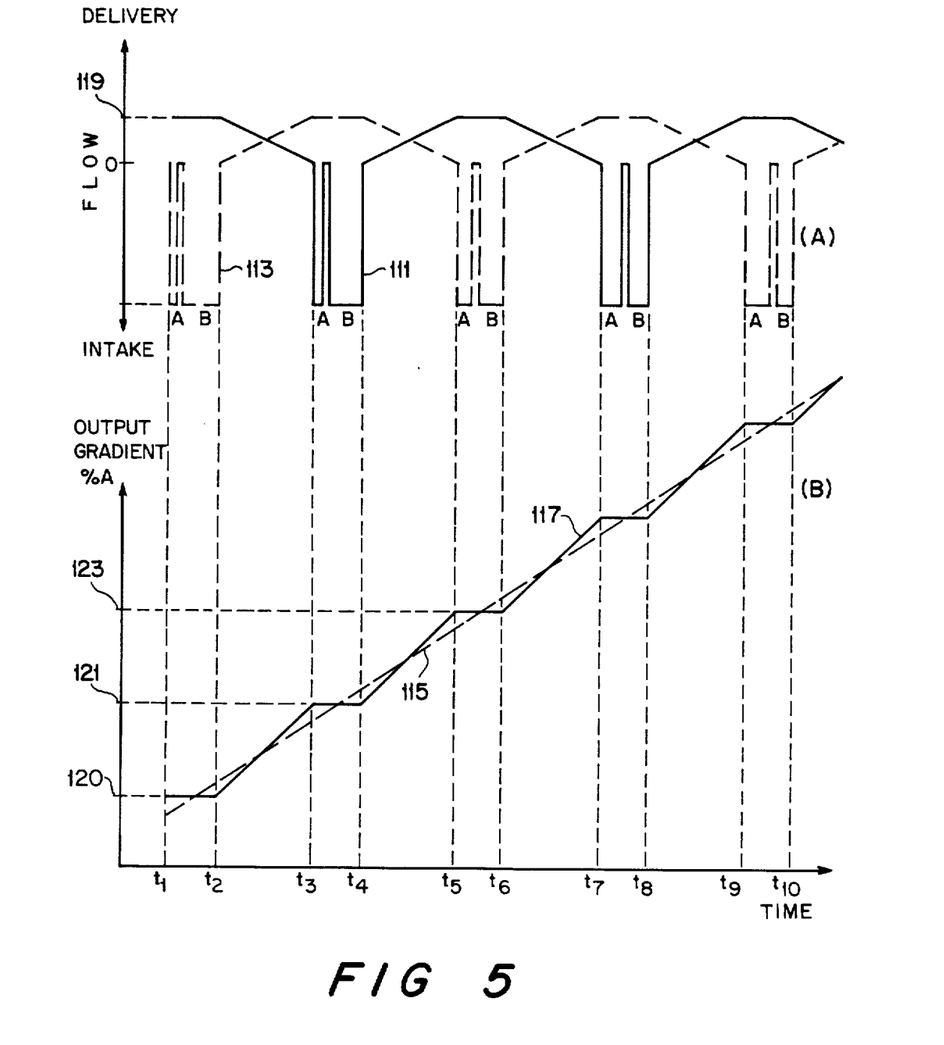
FIGS. 5 and 6 are curves which illustrate the operation of the mixing pump of FIG. 2, according with another specific embodiment thereof.
Figure 6:
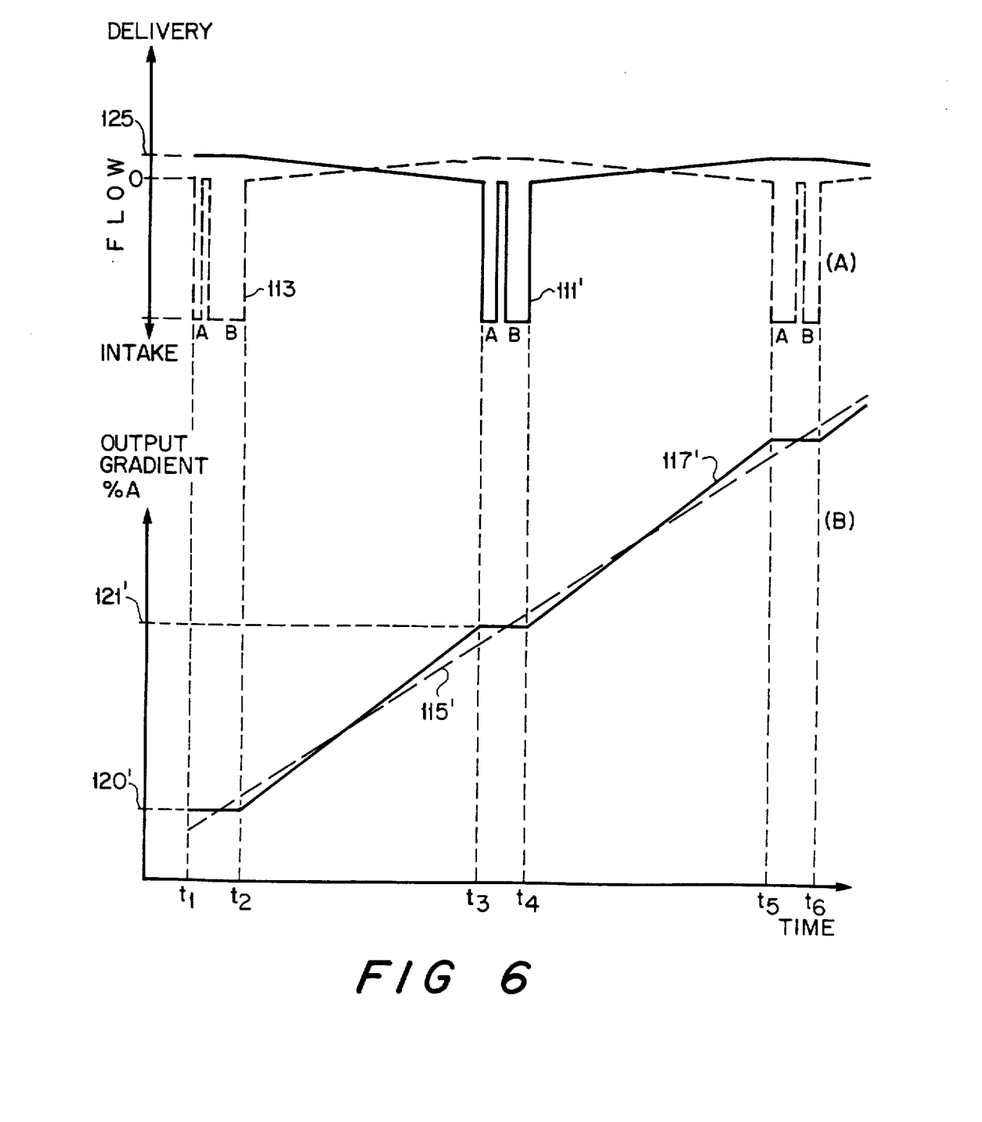

A second exemplary operable configuration for the improved mixing pumping system of FIG. 2 is illustrated in FIGS. 5 and 6. In this second example, the piston stroke lengths remain constant and the flow rate in the output 25 is adjusted by varying the velocity of the piston during the discharge portion of its stroke.

In both of these examples described below, the intake or charge time interval is constant for each of the displacement chambers, no matter what output flow is desired from the pump. Therefore, the same amount of time is provided for operation of the intake valves 57, 59 and 61 in order to assure accurately metered proportions of the different liquid components of the output mixture desired. Furthermore, as will better be seen from the following description of these two specific operable examples, the fixed chamber intake time allows a smoother gradient in the mixture in the output 25. These are significant improvements over the existing low pressure type mixing pump system. Subject to some constraints, the intake and discharge strokes may be optimized independently of each other since the pistons 43 and 45 are not mechanically locked to travel together.

Referring initially to FIG. 3, the first specific example will be described. FIG. 3(A) shows the flow into and out of each of the displacement chambers 39 and 41. Shown in a solid curve 91 is the flow through the conduit 47 of the chamber 39. Shown in a dashed curve 93 is, similarly, the flow in conduit 49 to and from the displacement chamber 41. In this example, it can be seen that the motors 77 and 79 are driving their respective pistons 43 and 45 essentially 180° out of phase with each other; that is, as one is filling its respective chamber, the other is discharging liquid from its chamber. A portion of each curve 91 and 93 above the middle "0" line shows a flow out of the respective displacement chamber, while that below the "0" line shows fluid flow into the respective chamber.

It will be noted from curve 91 of FIG. 3(A) that the valves 57 and 59 of FIG. 2 are operated so that the liquid solvent or component A from the container 11 is drawn into the chamber 39 for a certain portion of the intake cycle that is illustrated between times t1 and t2. During the remainder of the time the liquid component B is drawn into the chamber from the supply 17. In the examples shown in FIGS. 3-6, only two components A and B are assumed to be utilized, for simplicity in explanation, but it will be understood that additional liquid components can be introduced in the same manner, if desired.

Referring to FIG. 3(B), the relative proportions of the components A and B in the flow from the output 25 are illustrated. A dashed line 95 shows an ideal output gradient; that is, the ideally linear gradual change from, in this example, a low percentage of component A in the output mixture at the beginning, to a higher percentage of component A at a later time. A step function curve 97, however, reflects the actual variation in the composition of a mixture in the output 55. It is a step function since the composition of the pumps output can change only at times t1, t2, etc. The mixture of components A and B that are drawn into the chamber 91 during the time period t1-t2 is then discharged in the next time period t2-t3, that mixture being indicated at 99 on FIG. 3(B). Similarly, the mixture of components A and B drawn into the chamber 41 during the time period t2-t3 is that discharged from the output 55 during the next half-cycle, between times t3-t4, and is shown on FIG. 3(B) to have a percentage of component A indicated at 101.

A maximum intake flow indicated at 103 of FIG. 3(A), and a maximum discharge flow indicated at 105, is determined in this specific example by the displacement of the pistons in the respective chambers. The time interval for intake and discharge remains a predetermined fixed value. If it is desired to change that flow, as illustrated in FIG. 4, the piston stroke is adjusted accordingly. With reference to FIG. 4(A), for example, one-half the output flow rate is provided by shortening the piston stroke length by one-half. An output flow rate indicated at 107 is chosen, for this example, to be one-half of that indicated at 105 in FIG. 3(A). Of course, the intake stroke is also one-half of the previous example, a maximum intake flow rate indicated at 109. FIG. 4(A) is otherwise similar to FIG. 3(A).

It is extremely interesting to compare the output mixture gradient 97' of FIG. 4(B) with the gradient 97 of FIG. 3(B). They are identical since the intake and discharge times are, respectively, the same as that in the FIG. 3 example. The flat portion of the curve 97' of FIG. 4(B) remains the same as that of the curve 97 of FIG. 3(B). The output gradient does not depart any further from the ideal desired straight line 95 (95') when the output pump flow is decreased, contrary to the case in existing low pressure type mixing pumps.

The second specific operational example for the mixing pump 15 is described with respect to FIGS. 5 and 6, each of which is a curve showing information similar to that previously described with respect to FIGS. 3 and 4, but for fixed stroke, fixed intake time operating conditions. Referring initially to FIG. 5(A), the flow into and out of chamber 39 is indicated by a curve 111 in solid outline. Similarly, the flow into and out of the chamber 41 is shown by a curve 113 in dotted outline. In FIG. 5(B), a desired linear gradient change in the mixture at the output 25 is shown by a dashed line 115, the actual mixture as a function of time, for this specific embodiment, being shown as a solid line 117.

Between times t1 and t2, the pump of FIG. 2 is operating according to the specific example of FIG. 5 with its chamber 41 being charged with liquid constituents A and B in time sequence, as shown by curve 113 of FIG. 5(A), while the chamber 39 is discharging at a maximum rate 119, as indicated by the curve 111. During a time interval t2-t3, both of the chambers 39 and 41 are discharging, the one that has just been filled discharging at a gradually increasing flow rate while the chamber that had been discharging at a maximum rate during the interval t1-t2 now discharging at a gradually decreasing flow rate. The total flow from the two chambers, in this example, is maintained constant so that the flow rate at the output 25 of the pump is constant. The individual flows from the chambers need not necessarily be linearly increasing or decreasing, but the sum of the discharges from the two should be constant over time. This mixing makes the output composition gradually change from a level 120 to 121 in the interval t2-t3.

In the next interval of time t3-t4, the chamber 39 is being charged with a somewhat different mixture of liquid from the solvents A and B, the proportion of A being greater than during the chamber 41 fill of times t1-t2. At that same time, the chamber 41, as indicated by the curve 113, is discharging fluid at the maximum rate 119.

During the next interval of time t4-t5, both chambers are again simultaneously discharging through the common pump output 25, the one that has just been filled linearly increasing its flow, and the other decreasing its flow. The interval between time t1 and t5 constitutes a complete, single cycle of the pump's operation, which is then repeated.

The changing composition of the mixture at the output 25 is shown over the same time period in FIG. 5(B). The mixture (percentage of component A) being discharged during the time period t3-t4, indicated at 121, is the mixture that was drawn into the chamber 41 during the time period t1-t2. Similarly, the mixture at times t5-t6, indicated at 123, is that drawn into the chamber 39 during the previous fill interval t3-t4.

Referring to FIG. 6, the same basic operational example as FIG. 5 is given, except that the flow rate is reduced to one-half, while the desired gradient is the same. This reduced flow rate is indicated at 125 of FIG. 6. The reduced flow rate is accomplished by reducing the velocity of the piston during its discharge portion of its stroke, and this increases the time for discharge. The velocity and duration of the intake portion remain the same, as discussed previously. This means that the flat portions of the curve 117' of FIG. 6(B) remain of the same duration; that is, it is only during this fixed duration of the intake stroke of one chamber that liquid of unchanging composition is being discharged to the output 25 from the other chamber. This is an improvement over existing low pressure mixing pumps that increase the flat portions of their curves corresponding to curve 117' in the same proportion as the total pump cycle time.

There are many other variations of these two specific modes of operating the pump of FIG. 2 that are obviously available. For example, the velocity profile of piston movement during the intake stroke can be modified, such as stopping it during the portion of the stroke when the valves 57 and 59 are operated to switch from one liquid component to the other. This can provide greater precision in solvent proportioning. This is another advantage of uncoupling the two pistons of the displacement chambers, since without it, such a feature could not be implemented. Prior devices, with a common piston driving mechanism, would also stop the discharge flow for the period that the intake flow is stopped.

Another advantage of the separate piston motor drive is that the velocity profile of the piston during its delivery stroke can be modified to compensate for the compressibility of the liquid. This can be done without having to affect in any way the intake stroke.

The concepts of the present invention have been described as implemented in a liquid pump especially adapted for a liquid chromatograph. Of course, it will be understood, that the concepts have applicability in liquid pumps for other applications, particularly those with high precision requirements of liquid flow and mixture control. Also, the configuration of the pump described is also useful for mixing and pumping air and other gases. Further, it is useful for other substances that can be handled like fluids, such as slurries.

Although the various aspects of the present invention have been described with respect to preferred embodiments thereof, it will be understood that the invention is to be protected within the full scope of the appended claims.

It is claimed:

1. Apparatus for mixing and delivering fluid, comprising:

pumping means having at least two displacement chambers, including a first chamber and a second chamber, each chamber having a fluid intake and fluid output, independent sources of at least two fluids, including a first source and a second source, intake connecting means for connecting each of the fluid sources together to the fluid intakes of each of said chambers for providing a controllable proportion of said fluids from said sources to said intakes, said intake connecting means including means for connecting said first chamber to said first source and to said second source, said intake connecting means also including means for connecting said second chamber to said first source and to said second source, output connecting means for connecting the outputs of the chambers together for forming a single fluid output, and means connected to said displacement chambers for independently controlling the displacement in each of said chambers.

2. Apparatus according to claim 1 wherein exactly two displacement chambers are employed.

3. Apparatus according to claim 1 wherein said controlling means includes means for changing characteristics of fluid flow through the output of each of said at least two displacement chambers independently of the same characteristics of fluid flow through the intake of said chamber, whereby the characteristics of fluid intake and discharge can be independently optimized for each displacement chamber for a given flow rate without being restricted by the characteristics of the other for that chamber.

4. Apparatus according to claim 1 wherein said pump controlling means includes a means for maintaining a preselected time period of fluid intake during each cycle of operation of each of said two chambers and for adjusting the flow rate of fluid discharged from the chamber's output, whereby an intake cycle portion can be optimized for mixing the source fluids upon intake to each chamber and an output cycle portion thereof can be independently set for a desired fluid output.

5. Apparatus according to claim 4 wherein said controlling means additionally includes means for causing said chambers to simultaneously discharge fluid from their outputs through said single fluid output.

6. Apparatus accoridng to claim 5 wherein said controlling means additionally includes means for causing the fluid output of one chamber to gradually increase while causing the fluid output of the other chamber to gradually decrease during a time period of simultaneous fluid discharge from the chambers, the discharge of each chamber additionally being caused to be a maximum and substantially constant during the fixed intake time period of the other chamber.

7. Apparatus according to claim 4 wherein said fluid discharge adjusting means includes means for setting a maximum volume of displacement of said at least two chambers.

8. Apparatus for mixing and delivering fluid, comprising:

pumping means having at least two displacement chambers, including a first chamber and a second chamber, each chamber having a fluid intake and fluid output, independent sources of at least two fluids, including a first source and a second source, intake connecting means for connecting each of the fluid sources together to the fluid intakes of each of said chambers for providing a controllable proportion of said fluids from said sources to said intakes, said intake connecting means including means for connecting said first chamber to said first source and to said second source, said intake connecting means also including means for connecting said second chamber to said first source and to said second source, output connecting means for connecting the outputs of the chambers together for forming a single fluid output, and means connected to said displacement chambers for maintaining a preselected time period of fluid intake during each cycle of operation thereof and for adjusting the flow rate of fluid discharged from that chamber's output, whereby an intake cycle portion can be optimized for mixing the source fluids upon intake to each chamber and an output cycle portion thereof can be independently set for a desired fluid output.

9. A liquid chromatography system, comprising:

pumping means having at least two displacement chambers, including a first chamber and a second chamber, each chamber having a liquid intake and liquid output, independent liquid sources of at least two solvents, including a first source and a second source, intake connecting means for connecting each of the liquid sources together to the liquid intakes of each of said chambers for providing a controllable proportion of said liquid to said intakes, said intake connecting means including means for connecting said first chamber to said first source and to said second source, said intake connecting means also including means for connecting said second chamber to said first source and to said second source, output connecting means for connecting the chamber outputs together for forming a single liquid output, and means for changing characteristics of liquid flow though the output of each of said at least two displacement chambers independently of the same characteristics of liquid flow through the intake of said chamber, a sample injector positioned in the path of the single pumping means liquid output, a chromatograph column receiving the single pumping means output after passing though said sample injector, and a detector positioned at the output of said column.

* * * * *

UNITED STATES PATENT AND TRADEMARK OFFICE
CERTIFICATE OF CORRECTION

PATENT NO. : 4,714,545

DATED : December 22, 1987

INVENTOR(S) : H. Bryan Bente et al.

It is certified that error appears in the above-identified patent and that said Letters Patent is hereby corrected as shown below:

Column 5, line 13, "discarged" should read -- discarded --;

Column 9, line 57, "accoriding" should read -- according --;

Signed and Sealed this

Fifth Day of July, 1988

Attest:

DONALD J. QUIGG

Attesting Officer

Commissioner of Patents and Trademarks